United States Patent
Mohseni et al.

(10) Patent No.: US 11,099,000 B2
(45) Date of Patent: Aug. 24, 2021

(54) SYSTEMS FOR COHERENT LIGHT DETECTION AND RELATED METHODS

(71) Applicant: Northwestern University, Evanston, IL (US)

(72) Inventors: Hooman Mohseni, Wilmette, IL (US); Vala Fathipour, Berkeley, CA (US)

(73) Assignee: Northwestern University, Evanston, IL (US)

( * ) Notice: Subject to any disclaimer, the term of this patent is extended or adjusted under 35 U.S.C. 154(b) by 40 days.

(21) Appl. No.: 16/605,659

(22) PCT Filed: Apr. 13, 2018

(86) PCT No.: PCT/US2018/027572
§ 371 (c)(1),
(2) Date: Oct. 16, 2019

(87) PCT Pub. No.: WO2018/222282
PCT Pub. Date: Dec. 6, 2018

(65) Prior Publication Data
US 2020/0300604 A1   Sep. 24, 2020

Related U.S. Application Data

(60) Provisional application No. 62/486,722, filed on Apr. 18, 2017.

(51) Int. Cl.
*G01B 9/02* (2006.01)
*A61B 5/00* (2006.01)
*H01L 31/109* (2006.01)

(52) U.S. Cl.
CPC ........ *G01B 9/02091* (2013.01); *A61B 5/0066* (2013.01); *G01B 9/02004* (2013.01); *H01L 31/109* (2013.01)

(58) Field of Classification Search
None
See application file for complete search history.

(56) References Cited

U.S. PATENT DOCUMENTS

| | | | |
|---|---|---|---|
| 4,845,540 A * | 7/1989 | Baker | H01L 27/14643 348/297 |
| 7,745,816 B2 | 6/2010 | Mohseni | |
| 9,054,247 B2 | 6/2015 | Mohseni et al. | |

(Continued)

OTHER PUBLICATIONS

Fathipour, Vala, et al. "Impact of three-dimensional geometry on the performance of isolated electron-injection infrared detectors." Applied Physics Letters 106.2 (2015): 021116 (Year: 2015).*

(Continued)

*Primary Examiner* — Shawn Decenzo
(74) *Attorney, Agent, or Firm* — Bell & Manning, LLC

(57) ABSTRACT

Systems for coherent light detection are provided, including a system comprising a light source configured to generate light; a first optical assembly configured to split the light into a reference arm and a sample arm; a second optical assembly configured to illuminate a sample with light of the sample arm, thereby generating a sample signal; a third optical assembly configured to combine the sample signal with light of the reference arm, thereby generating an interference signal; and a detector assembly comprising an array of carrier injection photodetectors, the array arranged to collect the interference signal. Methods of using the systems are also provided.

22 Claims, 5 Drawing Sheets

(56) References Cited

U.S. PATENT DOCUMENTS

| | | | | |
|---|---|---|---|---|
| 10,121,819 | B2* | 11/2018 | Yao | H01L 27/14603 |
| 2010/0123120 | A1* | 5/2010 | Mohseni | H01L 27/14643 |
| | | | | 257/21 |
| 2013/0341594 | A1* | 12/2013 | Mohseni | B82Y 20/00 |
| | | | | 257/21 |
| 2014/0028997 | A1* | 1/2014 | Cable | H01S 5/0651 |
| | | | | 356/51 |

OTHER PUBLICATIONS

The International Search Report & Written Opinion issued in International Patent Application No. PCT/US2018/27572 dated Jan. 7, 2019, pp. 1-9.

Fechtig et al., "Line-field parallel swept source MHz OCT for structural and functional retinal imaging," Biomedical Optics Express, vol. 6, No. 3, Mar. 1, 2015, pp. 716-735.

Hardesty et al., Lecture—"Optical Remote Sensing with Coherent Doppler Lidar; Part 1: Background and Doppler Lidar Hardware," Apr. 4, 2011, pp. 1-42.

Jeehyun Kim, Dissertation—"Biomedical Imaging Applications of Parallel Optical Coherence Tomography and Adaptive Optics," The University of Texas at Austin, Dec. 2004, pp. 1-168.

Fathipour et al., "Isolated Electron Injection Detectors with High Gain and Record Low Dark Current at Telecom Wavelength," IEEE Journal of Selected Topics in Quantum Electronics, vol. 20, No. 6, Nov./Dec. 2014, pp. 1-6.

Movassaghi et al., "Analytical modeling and numerical simulation of the short-wave infrared electron-injection detectors," Applied Physics Letters, vol. 108, 2016, pp. 121102-1-121102-5.

Fathipour et al., "Demonstration of Shot-noise-limited Swept Source OCT Without Balanced Detection," Scientific Reports, published online: Apr. 26, 2017, pp. 1-9.

Fathipour et al., "Detector with internal gain for short-wave infrared ranging applications," Optical Engineering, vol. 56, No. 9, Sep. 2017, pp. 091608-1-091608-9.

Fathipour et al., "Electron-injection Detectors for Swept Source Optical Coherence Tomography," Optical Society of America, 2015, pp. 1-2.

* cited by examiner

SYSTEMS FOR COHERENT LIGHT DETECTION AND RELATED METHODS

CROSS-REFERENCE TO RELATED APPLICATIONS

This application is a National Stage of International Application No. PCT/US2018/027572, filed Apr. 13, 2018, which claims the benefit of U.S. Patent Application No. 62/486,722, filed Apr. 18, 2017, the contents of which are herein incorporated by reference.

REFERENCE TO GOVERNMENT RIGHTS

This disclosure was made with government support under W911NF-11-1-0390 awarded by the Army Research Office. The government has certain rights in the disclosure.

BACKGROUND

A number of imaging and sensing techniques involve coherent light detection. One such technique is optical coherence tomography, which provides images with micron-scale resolution and up to a few millimeters of tissue depth with the advantage of decoupling depth resolution from transverse resolution. Optical coherence tomography has become a workhorse in various fields such as biology, medicine, manufacturing inspection, and the physical sciences. In particular, optical coherence tomography has found applications as a diagnostic tool in ophthalmology, cardiology, dermatology, dentistry and in-situ biopsy.

Most high-speed optical coherence tomography imaging systems utilize swept source lasers (SS-OCT). This variation enables reduced sensitivity to patient motion, and allows deeper imaging compared with other optical coherence tomography schemes. Since the signal power produced by the photodetector in an optical coherence tomography system is proportional to the intensity of the reference beam, a high reference power is typically needed to amplify the signal above the detector noise. This requirement is even more significant when using swept source lasers due to the higher noise of fast photodetectors needed in a high-speed system. Since the intensity fluctuation noise power is also proportional to the square of the reference beam power, balanced detection is needed to cancel out the resulting intensity-fluctuation noise term. However, balanced detection requires a complex interferometer arrangement typically performed using fiber couplers and is quite challenging to implement in parallel optical coherence tomography schemes. Moreover, maintaining balanced performance across a wide spectral range to subtract out a large amount of intensity noise and other stringent requirements have limited parallel swept source optical tomography imaging schemes based on balanced detection.

A sensing technique involving coherent light detection is coherent LiDAR, which provides images of a target by illuminating the target with laser light and detecting the reflected light with a detector. In a coherent system, the reflected (returned) light is combined with a reference signal prior to detection.

SUMMARY

Provided herein are systems for coherent light detection and methods of using the systems, e.g., for performing optical coherent tomography and coherent LiDAR.

In one aspect, a system for coherent light detection is provided, the system comprising a light source configured to generate light; a first optical assembly configured to split the light into a reference arm and a sample arm; a second optical assembly configured to illuminate a sample with light of the sample arm, thereby generating a sample signal; a third optical assembly configured to combine the sample signal with light of the reference arm, thereby generating an interference signal; and a detector assembly comprising an array of carrier injection photodetectors, the array arranged to collect the interference signal. Each carrier injection photodetector comprises a semiconductor heterostructure comprising a photon absorber comprising a layer of photon absorbing material selected to absorb photons to generate electron-hole pairs therein; and a carrier injector configured to inject one of either electrons or holes into the photon absorber, the carrier injector comprising a layer of carrier injecting material selected to generate the one of either electrons or holes upon application of a bias voltage across the carrier injection photodetector and a carrier trap between the layer of carrier injecting material and the layer of photon absorbing material, the carrier trap comprising a layer of potential barrier-forming material selected to form a potential trap for the other of either electrons or holes generated in the photon absorber.

In an embodiment, a system for parallel, line scan optical coherence tomography is provided, the system comprising a light source configured to generate light, wherein the light source is a swept-source laser; a first optical assembly configured to split the light into a reference arm and a sample arm; a second optical assembly configured to illuminate a sample with light of the sample arm, thereby generating a sample signal; a third optical assembly configured to combine the sample signal with light of the reference arm, thereby generating an interference signal; and a detector assembly comprising a linear array of carrier injection photodetectors, the array arranged to collect the interference signal. Each carrier injection photodetector comprises a semiconductor heterostructure comprising a photon absorber comprising a layer of photon absorbing material selected to absorb photons to generate electron-hole pairs therein; and a carrier injector configured to inject one of either electrons or holes into the photon absorber, the carrier injector comprising a layer of carrier injecting material selected to generate the one of either electrons or holes upon application of a bias voltage across the carrier injection photodetector and a carrier trap between the layer of carrier injecting material and the layer of photon absorbing material, the carrier trap comprising a layer of potential barrier-forming material selected to form a potential trap for the other of either electrons or holes generated in the photon absorber.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the disclosure will hereafter be described with reference to the accompanying drawings.

DETAILED DESCRIPTION

Figure 1:
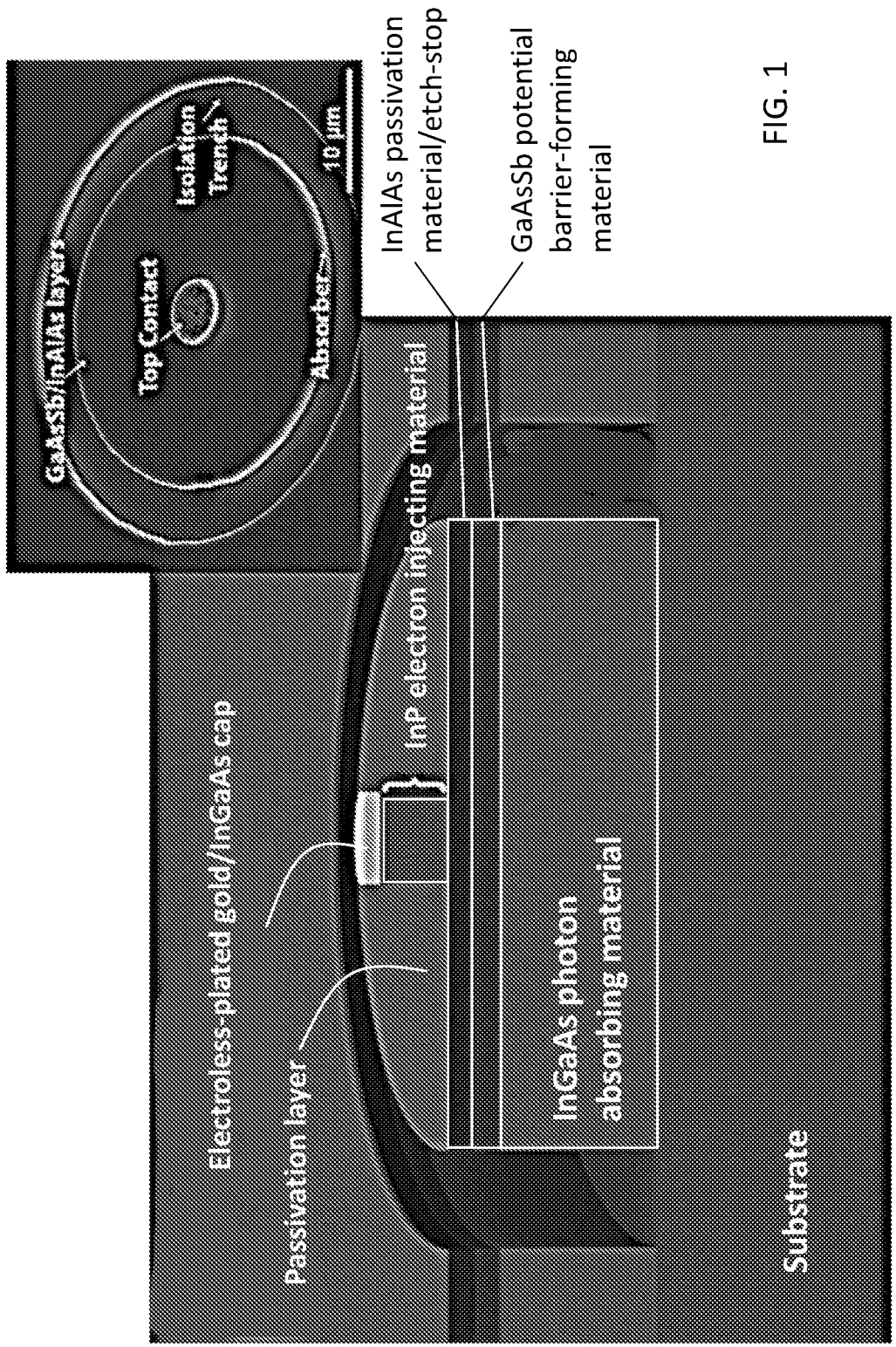
FIG. 1 is a schematic diagram of a passivated electron injection (EI) photodetector with a 5 µm electron injector diameter and a 30 µm photon absorber diameter. The scanning electron microscope image shown at the top of FIG. 1 was taken before passivation and electroless plating.

Provided herein are systems for coherent light detection and methods of using the systems, e.g., for performing optical coherence tomography and coherent LiDAR. The systems and methods involve the use of electron injector (EI) photodetectors. Although EI photodetectors are known to exhibit high gain, it is also known that the gain (and speed) for the EI photodetectors drops precipitously as sample signal decreases. (See, e.g., Applied Physics Letters 106 (2), 021116, 2015.) Thus, it has not been evident that EI photodetectors could be used to detect weak sample signals, such as those generated in optical coherence tomography and coherent LiDAR. The present disclosure is based on the inventors' findings that a reference signal, which is combined with a sample signal in coherent light detection, unexpectedly overcomes the problem of prohibitively low gain/speed of EI photodetectors.

Advantages of at least some embodiments of the present systems and methods include one or more of: eliminating any need for balanced detection; very small power of light from reference arm per individual EI photodetector required; and eliminating any need for fast low-noise amplifiers.

In one aspect, systems for coherent light detection are provided. In a basic embodiment, such a system comprises a light source configured to generate light; a first optical assembly configured to split the light into a reference arm and a sample arm; a second optical assembly configured to illuminate a sample with light of the sample arm, thereby generating a sample signal; a third optical assembly configured to combine the sample signal with light of the reference arm, thereby generating an interference signal; and a detector assembly comprising an array of EI photodetectors, the array arranged to collect the interference signal.

Depending upon the application, different light sources may be used. However, generally, the light source is one which emits light having a wavelength in the near-infrared region (i.e., from about 750 nm to about 1 μm) or in the short-wave-infrared region (i.e., from about 1 μm to about 2.5 μm) of the electromagnetic spectrum. The light source may be a broadband light source configured to emit its light over a broad range of frequencies (e.g. spanning 10% of the center frequency). Typically, lasers are used as the light source. The light source may be a swept wavelength tunable laser, i.e., a swept-source laser such as a vertical-cavity surface emitting laser (VCSEL). Chirped lasers may be used, e.g., for coherent LiDAR. Also pulsed lasers can be used, due to their similarly broad spectral content. Light emitting diodes (LED) and Superluminescent Light Emitting Diodes (SLEDs, SLDs) could also be used in optical coherence tomography. Supercontinuum lasers can be used in both coherent LiDAR and optical coherence tomography.

A variety of components may be used in the first, second and third optical assemblies, the components selected and arranged so that the assemblies can perform the desired function of splitting a light beam, illuminating a sample, and combining multiple light beams, respectively. Such components include beam splitters, directional couplers, fiber optics, lenses, etc. Mirrors, filters, etc. may also be included in one or more of the optical assemblies. Different optical assemblies may share some of the same components. Regarding illuminating the sample, illumination is not limited to a typical "spot," but illumination regions may be in the form of a line spanning a relatively larger area of the sample. This is useful, e.g., for parallel, line field optical coherence tomography.

The EI photodetectors in the array of the detector assembly are semiconductor heterostructures which comprise a photon absorber comprising a layer of photon absorbing material; and an electron injector configured to inject electrons into the photon absorber. The photon absorbing material is a semiconductor material selected to absorb photons of a particular wavelength to generate electron-hole pairs therein. The electron injector comprises a layer of electron injecting material and an electron trap between the layer of electron injecting material and the layer of photon absorbing material. The layer of electron injecting material is a semiconductor material selected to generate electrons upon application of a bias voltage across the EI photodetector. The electron trap comprises a layer of potential barrier-forming material. The layer of potential barrier-forming material is a semiconductor material selected to form a potential trap for holes of the electron-hole pairs generated in the photon absorber. Other layers may be included on and/or within the semiconductor heterostructures, e.g., a layer of a passivating material, a semiconductor material selected to minimize surface states or other external fields from penetrating into the electron injection photodetectors. Passivating materials which are included within the semiconductor heterostructures, e.g., between the layer of electron injecting material and the layer of potential barrier-forming material may also serve as an etch stop layer during fabrication. The semiconductor heterostructure may further include a cap layer over the electron injector. The cap layer may be composed of a semiconductor material selected to facilitate electrical communication with the layer of electron injecting material.

The materials used for the various layers of the EI photodetectors and the thicknesses of those layers may be broadly selected, depending upon the application as well as the desired performance characteristics (e.g., gain, bandwidth, quantum efficiency, dark count, etc.). The various layers may be doped or undoped as needed depending upon the application and desired performance characteristics. Illustrative materials include Group III-V semiconductors, such as InP- and GaAs-based materials and Group II-VI semiconductors, such as CdTe-based materials.

EI photodetectors may be fabricated which have high gains, large bandwidths, high quantum efficiencies and low dark counts. However, in embodiments of the present systems and methods, EI photodetectors having more modest values for one or more these properties may be used. An illustrative gain exhibited by the EI injection photodetectors of the array of EI photodetectors includes a gain in the range of from 50 to 2000 at a bias voltage of 1 to 3 Volts, at a wavelength of 900 nm to 1700 nm at room temperature. An illustrative bandwidth exhibited by the individual EI photodetectors of the array of EI photodetectors includes a bandwidth in the range of from 5 MHz to 1 GHz. However, in view of the unexpected advantage that the use of a reference signal overcomes the problem of low gain/speed when detecting weak sample signals, EI photodetectors having relatively smaller gains and bandwidths may be used. In embodiments, the gain exhibited by the EI injection photodetectors of the array of EI photodetectors is less than 300, less than 200, or less than 100 at a bias voltage of 1 to 3 Volts, at a wavelength of 900 nm to 1700 nm at room temperature. In embodiments, the bandwidth exhibited by the individual EI photodetectors of the array of EI photodetectors is less than 100 MHz, less than 50 MHz, or less than 10 MHz. These performance characteristics may be determined using the techniques described in U.S. Pat. No. 9,054,247, which is hereby incorporated by reference in its entirety.

An illustrative, individual EI photodetector is shown in FIG. 1, with the material layers labeled. Additional details about the compositions of the material layers and the thicknesses of the layers are provided in the Example, below. In this embodiment, the selection of the materials for the photon absorbing material, the electron injecting material and the potential barrier-forming material is such that the semiconductor heterostructure has a band structure with a type-II band alignment. However, other selections providing other band structures may be used.

Also, in this embodiment, the carrier injecting material has been processed to form a pillar having a diameter of about 5 µm. The photon absorbing material has been processed to form a larger pillar having a diameter of about 30 µm. Although the maximum lateral dimension of the carrier injecting material will generally be smaller than the maximum lateral dimension of the photon absorbing material, various lateral dimensions may be used. The "maximum edge-to-edge dimension" refers to the distance measured along a plane parallel to the material layers of the semiconductor heterostructure. Since other shapes besides cylindrical pillars may be used, "dimension" is used instead of "diameter." Although minimizing the lateral dimension of the carrier injecting material provides smaller electron injectors and can improve gain and suppresses dark count, the present systems and methods may make use of individual EI photodetectors having carrier injecting materials characterized by maximum edge-to-edge dimensions on the order of microns (1 µm or greater), rather than nanometers (less than 1 µm). This includes a maximum edge-to-edge dimension of at least about 5 µm, at least about 10 µm, or in the range of from about 5 µm to about 50 µm. Other individual EI photodetectors may be used, including those described in U.S. Pat. No. 9,054,247, which is hereby incorporated by reference in its entirety.

It is to be understood that the term "electron" in "electron injector photodetector" can be changed to "hole" to provide an analogous "hole injector photodetector." Thus, the term "carrier" may be used to encompass photodetectors in which the carriers which are injected are one of electrons and holes and similarly, in which the carriers which are trapped are the other of electrons and holes.

As noted above, the present systems and methods make use of arrays of individual EI photodetectors. In embodiments, the array is a linear array, i.e., a plurality of individual EI photodetectors arranged in a line. Within such a linear array, an individual EI photodetector may be considered a channel. Linear arrays having a variety of numbers of channels may be used, e.g., 10 channels, 16 channels, 64 channels, 1024 channels. An additional channel may be included in each of these arrays (e.g., 10+1=11 channels) to produce a K-clock as further described below with respect to FIG. 2. In embodiments, the array is a two-dimensional array.

Figure 2:
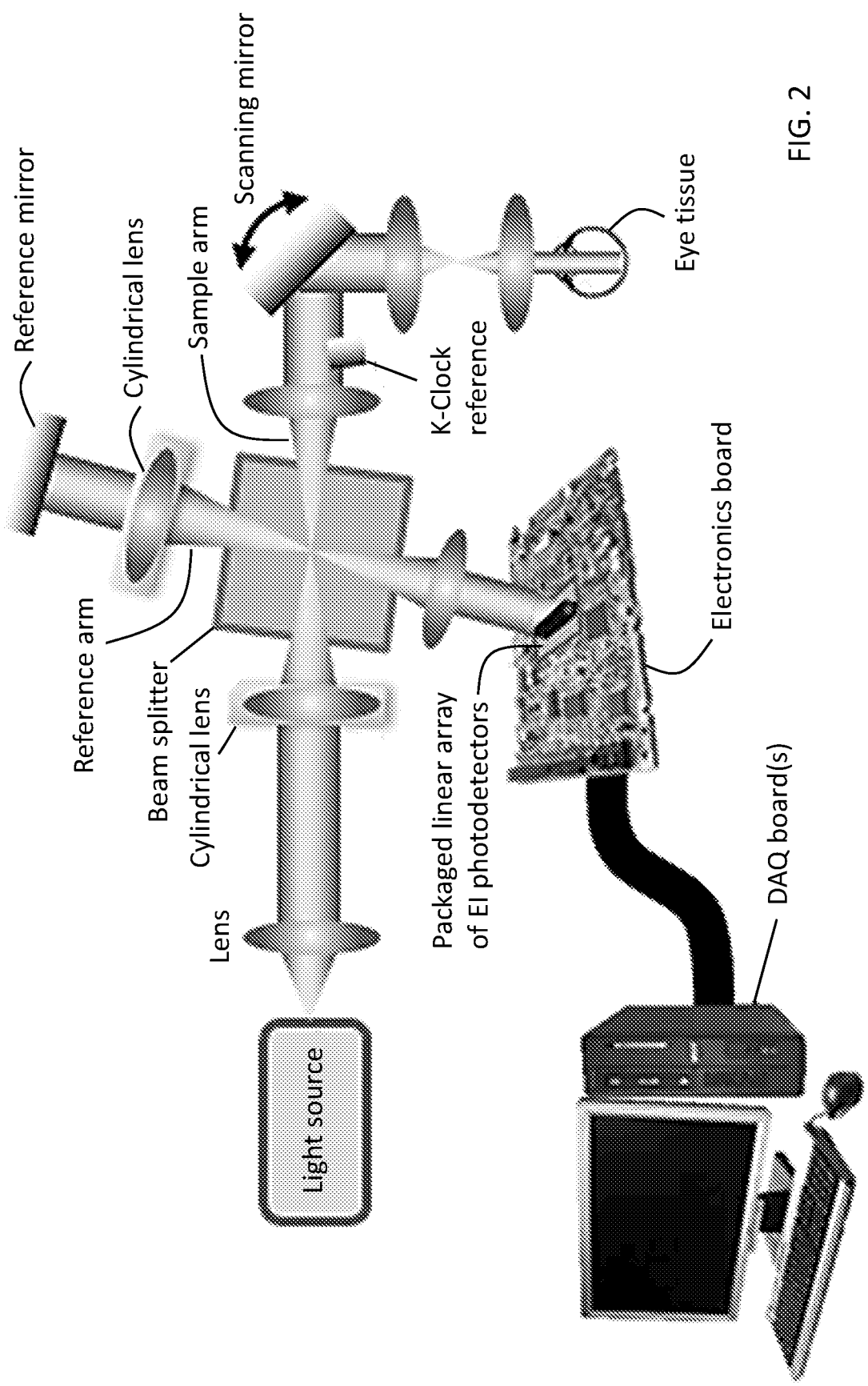
FIG. 2 shows a schematic of a system configured to perform optical coherence tomography according to an illustrative embodiment.

The present systems may comprise a variety of other components, e.g., computers, electronic circuit boards, amplifiers, data acquisition boards, etc., the selection of which depends upon the particular application for the system. In embodiments, the system is configured to perform optical coherence tomography on the sample, including parallel, line scan optical coherence tomography. An illustrative embodiment of a system configured to perform parallel, line scan optical coherence tomography is shown in FIG. 2. The system includes a light source, which may be a swept-source laser producing light which is split into a reference arm and a sample arm using suitable optical components. Suitable optical components are used to illuminate a sample (e.g., the tissue of an eye), with light of the sample arm. The illuminated region on/within the sample may be a line as described above. The illumination generates a sample signal, which is combined with light from the reference arm using suitable optical components to generate an interference signal (e.g., an interference line). The system includes a detector assembly comprising a linear array of EI photodetectors arranged to collect the interference line. In this embodiment, the linear array of EI photodetectors is packaged in a ceramic leadless chip-carrier. The package has an optical window and is mounted on an electronics circuit board. The optical components shown in FIG. 2 are further configured so that a portion of the light of the sample arm travels a fixed path-length to produce a K-clock. Amplified interferograms of all channels (i.e., individual EI photodetectors) and the K-clock are fed into multi-channel data acquisition boards. The system further comprises a computer programmed to control the system components and to process collected data from the linear array of EI photodetectors into live optical coherent tomographic images in real time.

In embodiments, the system is configured to carry out coherent LiDAR on a far object (the sample). The basic components of such a system include those described above with respect to the basic embodiment of the present system. However, the system may include other components typically used in coherent LiDAR sensing, such as different optics designed for long operating range and different light sources as described above. Also, the system may use guided light (e.g. fiber optics, couplers, and circulators) instead of the free-space configuration described herein.

Figure 3:
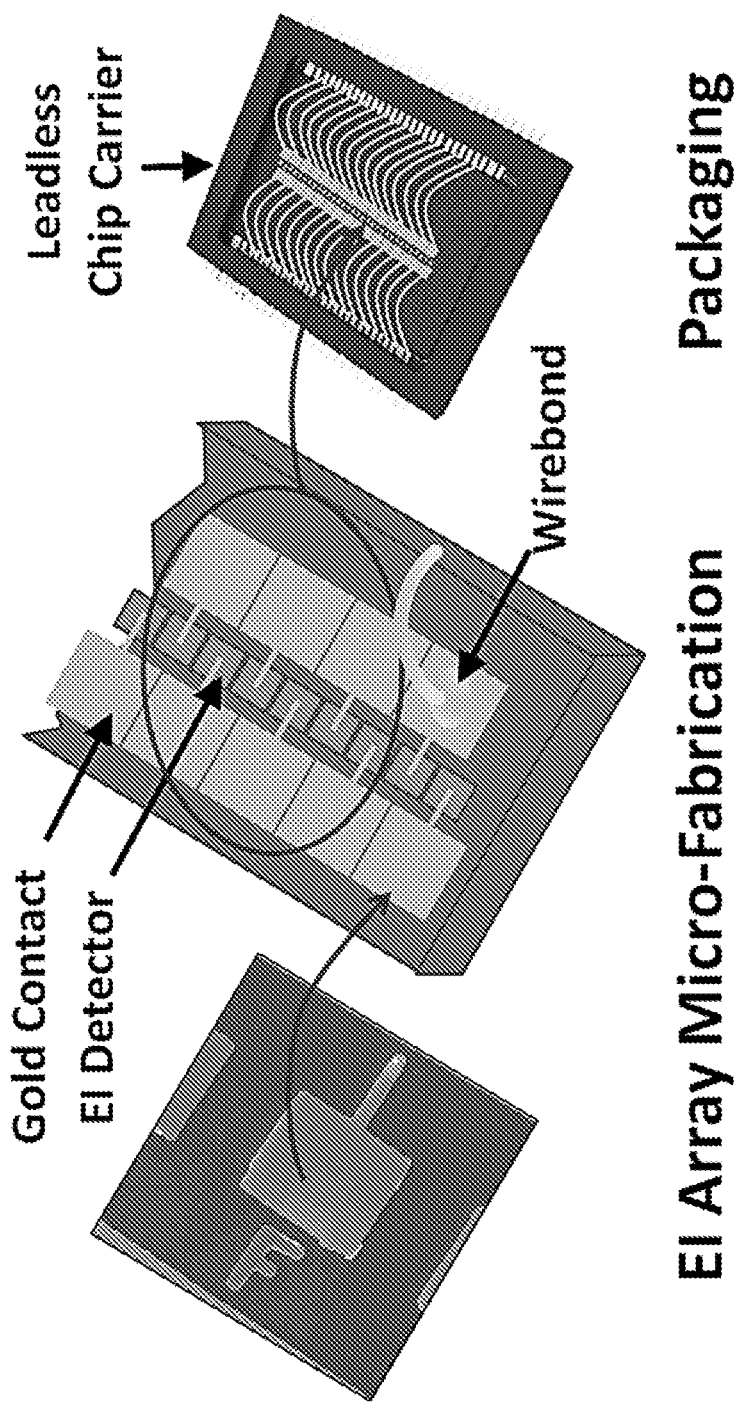
FIG. 3 shows a wire-bonding method used in fabricating a linear array of EI photodetectors.

Illustrative methods of making individual EI photodetectors are described in the Example below, and in U.S. Pat. No. 9,054,247, which is hereby incorporated by reference in its entirety. The methods may be modified as follows for fabricating the arrays of EI photodetectors, including linear arrays. Briefly, an epitaxial wafer may be processed using micro-fabrication tools. Micron- or nano-sized electron injectors may be formed by e-beam patterning the samples, depositing thin metal films on the patterned substrate and using the thin films as a hard mask in the etching process. The array of passivated devices may then be planarized using a spin-on polymer, which then may be partly removed in an etch-back process to expose the top metal layer on the electron injectors. Finally, a larger contact may be evaporated on the top of the planarized electron injectors. Indium bumps may be formed on top of each photodetector contact, and a transparent sapphire substrate with metal fan-out patterns may also be formed. The chip having the array of EI photodetectors and the sapphire fan-out chip may be bonded using a custom-built ultra-accurate flip-chip bonder (see Fathipour, V., et al., "Advances on Sensitive Electron-Injection Based Cameras for Low-Flux, Short-Wave Infrared Applications," *Front. Mater.*, Aug. 5, 2016). However, as an alternative to flip-chip bonding, a wire-bonding method may be used. The wire-bonding method is illustrated in FIG. 3 showing that an array of EI photodetectors may be packaged in a leadless chip carrier and a conventional wire-bonding method used to connect top contacts of individual EI photodetectors to pins of the leadless chip carrier.

In another aspect, methods of using the present systems are also provided. In a basic embodiment, such a method comprises splitting light from a light source into a reference arm and a sample arm; illuminating a sample with light from the sample arm, thereby generating a sample signal; combining the sample signal with light from the reference arm, thereby generating an interference signal; and collecting the interference signal on an array of EI photodetectors. The method may be carried out on any of the systems described herein, including using any of the arrays of EI photodetectors described herein. Depending upon the configuration of the system as described above, the method of using the system achieves a particular imaging or sensing technique, e.g., parallel line scan optical coherent tomography or coherent LiDAR sensing. The present systems may also be used as a coherent receiver in optical data links.

EXAMPLE

Introduction

In this example, an EI photodetector was used to demonstrate the shot-noise-limited sensitivity in a swept source optical tomography (SS-OCT) system without balanced detection and at room temperature. Shot-noise-limited performance was achieved at what is thought to be the lowest reference power level reported in a SS-OCT system.

The EI photodetector has a very large internal amplification [43, 23] that enhances the signal well above the receiver electronic noise, even for a reference beam power of ~350 nW. The results are compared with those of a commercial p-i-n detector that was measured simultaneously in the same setup. Theoretical calculations showed excellent agreement with the experimental results.

This approach can immediately address the demand for a portable OCT system, which has been the subject of much recent scientific attention [24, 25, 26, 27]. It eliminates the concomitant complexity and size of typical OCT systems. In addition to eliminating many passive components required for a balanced detection scheme, the low power requirement of this approach allows replacing the typical large-footprint high-power OCT laser sources with an electrically pumped tunable VCSEL [41,42] to radically reduce the size and cost of OCT systems.

Methods

EI Photodetector Layer Structure and Fabrication Procedure.

The current device is composed of 1000 nm of n doped $In_{0.53}Ga_{0.47}As$ absorber, 50 nm of $p^+$ doped $GaAs_{0.52}Sb_{0.48}$ trapping layer, 50 nm of undoped $In_{0.52}Al_{0.48}As$ etch-stop layer, 500 nm of $n^+$ doped InP injector, and 50 nm $n^+$ doped $In_{0.53}Ga_{0.47}As$ cap layer. Layers were grown by metal organic chemical vapor deposition on 2-inch InP substrates [43].

Devices were fabricated by patterning the wafers with e-beam lithography to form the contact metals. Conventional metallization with an E-beam evaporator was used to lift off multi-layer metal contacts, which act as a hard mask for reactive ion etching with $CH_4/H_2$ chemistry to form the injector pillars. Wet etching of InAlAs and GaAsSb followed by a $CH_4/H_2$ dry etching of InGaAs was then used to define the absorber volume. Finally, the detectors were passivated. For robust direct probing of detectors, electroless plating was used to convert the top Nickel contact to gold. FIG. 1 shows a schematic of the EI photodetector with a 5 μm electron injector diameter and a 30 μm absorber diameter that was used in this experiment. A scanning electron microscope image is shown in the inset of FIG. 1, before passivation. All results reported here are based on devices operating at room temperature.

Details of Noise Equivalent Power (NEP) Measurement Setup Equipment.

A 1550 nm DFB, Butterfly laser from JDSU was biased through a DC source. A function generator (Gigatronics 6061A) provided the small signal swing. A bias-T (ZFBT-6GW from Mini-Circuits) was utilized to separate DC bias from the small signal AC signal. A 1550 nm 2×2 coupler (from Thorlabs) was utilized to send the modulated optical signal to the EI photodetector and a p-i-n detector simultaneously. A digital attenuator with 0.01 dB accuracy (NIST calibrated) was used in order to be able to vary the power on the EI photodetector. The frequency response was recorded using a real-time scope with a 2.5 GHz bandwidth (Agilent Technologies MSO254A). For the noise measurement, a spectrum analyzer from Anritsu (Anritsu MS2717A) was utilized.

Details of SS-OCT Setup Equipment.

Figure 4:
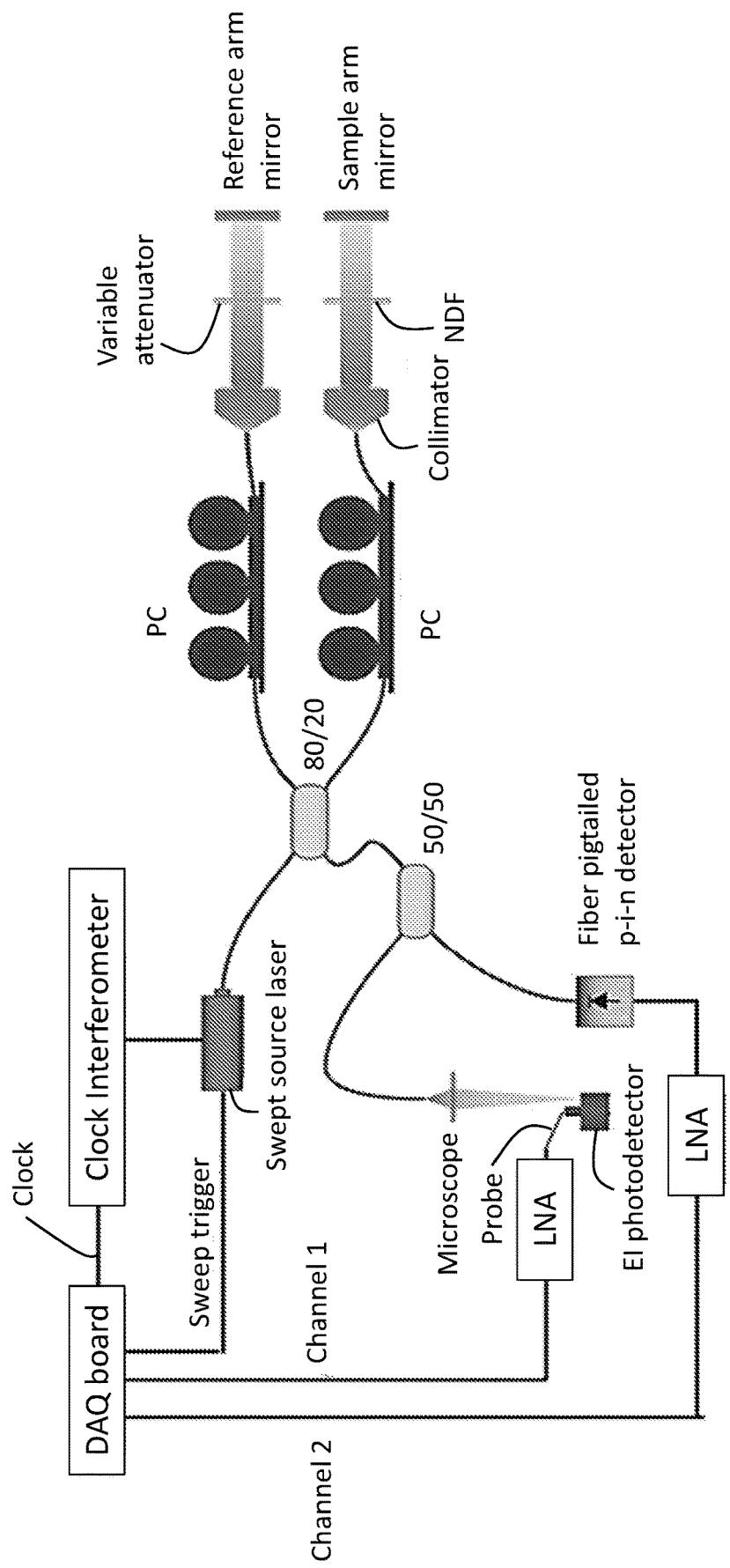
FIG. 4 shows a schematic diagram of an optical coherence tomography measurement setup using a swept source laser for comparing an individual EI photodetector with a commercial p-i-n detector. The swept source laser has a central wavelength of 1060 nm, with 110 nm tuning range and 100 kHz scan rate. In order to be able to properly compare the signal-to-noise ratio (SNR) performance of the EI photodetector and the commercial fiber pigtailed p-i-n detector, a second directional coupler (50/50) was used to simultaneously send the interference signal to both detectors. Light was coupled to the EI photodetector via a microscope set up, which added optical loss. NDF: Natural Density Filter, PC: Polarization Controller, LNA: Low Noise Amplifier, DAQ: data acquisition board.

The experimental set-up is shown in FIG. 4. The swept laser source (from Axsun Technologies) was followed by an (AC Photonic, Inc) optical isolator. The light output was then launched into a 2×2 coupler (from Thorlabs). The sample and reference arms were arranged with fiber collimators and mirrors. The mirrors and collimators were mounted on (KM100-Mount from Thorlabs) kinematic stages to allow coupling back to fibers. To alter the polarization of the transmitted light in the single mode fibers, two 3-Paddle Polarization Controllers (from Thorlabs) were utilized on the sample and reference arm fibers. The interference signal from the sample and reference arms was incident on the commercial p-i-n detector as well as the electron-injection detector. Outputs of the p-i-n and the EI photodetectors were amplified simultaneously using (DUPVA 1-70) low-noise voltage amplifiers (from Femto). Electronic band-pass filtering was implemented using (250 MHz low pass filter from Mini-Circuits and 2 MHz high pass filter from TTE Filters), to improve the SNR. Data was digitized using a data acquisition board (ATS9350, Alazar Technologies, Inc.) with a 12-bit resolution and a sampling rate of 500 mega samples per second. In the first step, for each channel, a total of 1376 data points were obtained on each wavelength sweep. Background spectrum of each channel was also obtained using 1376 data points. After subtraction of background spectrum, the resulting spectrum was reshaped by a Hann window and an inverse discrete Fourier transformed to give a single depth profile of the sample.

Theoretical Analysis.

As illustrated in FIG. 4, the interference signal that resulted from the mixing of the reference and the sample arm beams, which carried the information of interest, was incident on the EI photodetector. To obtain a relation for the EI photodetector's current, it was assumed that the sample mirror was located at the axial coordinate $z=z_0$, and $z=0$ corresponded to a zero optical path length difference between the two interferometric arms. The current of a detector with internal amplification G, which is detecting the interference signal as (1), is expressed as follows:

$$i_{detector}(t) = \frac{\eta q}{h\nu} \cdot \left[ G \cdot P_r + G \cdot P_0 \cdot r(z_0)^2 + 2 \cdot G \cdot \sqrt{P_0 \cdot r(z_0)^2 \cdot P_r} \cdot \cos(2k(t)_{z_0} + \varphi(z_0)) \right] \quad (1)$$

As indicated in (1), the internal amplification G effectively boosted the weak signal reflected from the sample, even if the reference signal was not strong. In (1), $r(z_0)^2$ denotes sample arm reflectivity; $\varphi(z_0)$ is the interferometric phase shift associated with the detector signal;

$$k(t) = \frac{2\pi}{\lambda(t)}$$

is the wave number, which is varied in time monotonically by tuning of the laser; $P_r$ is the time average optical power over one tuning cycle from the reference arm at the detector; $P_0$ is the time average optical power over one tuning cycle illuminating to the sample arm. The term $$\frac{\eta q}{h\nu}$$

denotes the current to power conversion factor, where $\eta$ is the quantum efficiency, $h\nu$ is the photon energy, and q is the electron charge. The first and second terms in (1) contribute to the non-interference background and the third term represents the interferometric signal. The detector's signal current, $i_s(t)$, and noise power, $i_n^2(t)$ are expressed as (2) and (3) respectively:

$$i_s(t) = \frac{\eta q}{h\nu} \cdot G \cdot 2 \cdot \sqrt{(P_s \cdot P_r)} \cdot \cos(2k(t)z_0) \quad (2)$$

$$\langle i_n^2(t) \rangle = i_{shot-photon}^2 + i_{RIN}^2 + i_{amp}^2 \quad (3)$$

In (2), $P_s = P_0 \cdot r^2$ denotes the optical power reflected from the sample at the detector with the condition $P_s \ll P_r$. In (3), brackets < > denote a time average. The total noise current of detector is composed of the noise current due to the statistical nature of incoming photons ($i_{shot-photon}$) expressed as (4); the intensity fluctuation noise term ($i_{RIN}$) expressed as (5); and the electrical noise from the post-detection circuitry, which is dominant at low reference power levels ($i_{amp}$).

$$i_{shot-photon} = \left( 2 \cdot q \cdot \frac{\eta q}{h\nu} \cdot G^2 \cdot (P_r + P_s) \cdot BW \cdot F \right)^{1/2} \quad (4)$$

$$i_{RIN} = \left( P_{RIN} \cdot \left(\frac{\eta q}{h\nu}\right)^2 \cdot G^2 \cdot (P_r + P_s)^2 \cdot BW \cdot F \right)^{1/2} \quad (5)$$

where, $P_{RIN}$ is the relative intensity noise given in unit of $Hz^{-1}$, BW is the detection bandwidth, and F is the excess noise factor, which is a measure of deviation from the predicted shot noise level. The signal-to-noise ratio of the electron-injection detector is thus expressed as (6):

$$(SNR)_{EI} = \frac{\langle i_s^2(t) \rangle}{\langle i_n^2(t) \rangle} = \frac{2 \cdot \left(\frac{\eta q}{h\nu}\right)^2 \cdot (P_s P_r) \cdot G^2}{\left[ i_{amp}^2 + 2q \cdot \frac{\eta q}{h\nu} \cdot G^2 \cdot (P_r + P_s) \cdot F + P_{RIN} \cdot \left(\frac{\eta q}{h\nu}\right)^2 \cdot G^2 \cdot F(P_r + P_s)^2 \right] \cdot BW} \quad (6)$$

The sensitivity is defined as the reflectivity that produces a signal power equal to the noise power, and under shot-noise limited operation, is described by equation (7):

$$(Sensitivity)_{EI}[dB] = -10 \log \frac{\eta P_0}{h\nu \cdot BW} \quad (7)$$

Experimental Results and Discussion

This Example evaluated the performance of an EI photodetector utilized in a swept source OCT system. EI photodetectors utilize a similar device micro-processing and material system as the conventional p-i-n photodiodes (see Methods). The EI photodetectors used in this Example have a cutoff wavelength of 1700 nm when operated at room temperature. EI photodetectors with shorter cutoff wavelengths have even better noise performance.

Experimentally Measured Noise Equivalent Power of EI Photodetectors.

Outside the shot-noise-limit, improving the noise equivalent power (NEP) of the photon detector has a significant impact on the OCT system performance. This is because the system sensitivity improves with the square of the detector NEP. Under shot-noise-limited conditions, reducing NEP leads to a reduction of the required reference power. Therefore, in order to evaluate the use of EI photodetectors in an SS-OCT system, the noise equivalent power of the EI photodetector was measured and compared to the state-of-the art balanced photodetectors at frequencies relevant to high-speed SS-OCT systems. To obtain the NEP, the well-known formula NEP=$I_n/\mathcal{R}$ was used. In this equation, $\mathcal{R}$ is the detector responsivity, and $I_n$ is the spectral noise of the detector. A small-signal homodyne measurement approach was used (schematic not shown) to measure EI photodetector responsivity from 100 KHz to 250 MHz. In this setup, a DC voltage source was used to provide the bias voltage for the tunable laser, and a function generator was used to provide the small-signal voltage swing. The monitoring p-i-n detector ensured delivery of constant optical power to the EI photodetector at all frequencies. The spectral noise of the EI photodetector was further measured in the same setup using a spectrum analyzer. The extracted noise equivalent power of the EI photodetector was obtained (data not shown). The NEP of the EI photodetector was as low as 300 fW/√Hz at room temperature. Since the EI photodetector was not a packaged device, the EI photodetector was probed inside a microscope setup. The high-frequency peaks observed were due to the background radio signals picked up by the un-shielded probe.

It is worth noting that since the conception of OCT, the detectors used in these systems have not seen considerable improvement. In fact, the noise equivalent powers of balanced detectors with bandwidths of higher than 100 MHz have been nearly constant (at about ~3-10 pW/√Hz), over the past 20 years [17, 18, 33, 31, 32]. The better NEP of the EI photodetector suggests that for the same reference arm power, the minimum detectable OCT signal using the balanced detectors would be more than two orders of magnitude worse than the EI photodetector. Equivalently, to obtain the same sensitivity, more than two orders of magnitude higher reference arm power is needed for the balanced detectors approach.

SS-OCT Experimental Setup.

Next, the performance of the EI photodetector was evaluated in an actual SS-OCT setup. FIG. 4 shows a schematic diagram of this system. The output of a swept laser source was split via a directional coupler (splitting ratio 80/20), into the reference arm and the sample arm, which illuminated and received the light reflected from the sample. A single reflector (mirror) and a neutral density filter (NDF) were used to mimic the sample. The reference power was varied by means of a variable neutral density filter placed in front of the reference arm reflector. The swept source laser had a sweep rate of 100 KHz and a center wavelength of 1060 nm. The theoretical limit for the free space axial resolution, and ranging depth are 4.9 μm and 3.7 mm, respectively, in this setup.

The interference between the reference arm and sample arm signals was detected with the EI photodetector. In order to properly compare the SNR performance of the EI photodetector and a commercial p-i-n detector, a second directional coupler (splitting ratio 50/50) was used to simultaneously send the interference signal to both devices. Light was coupled to the EI photodetector via a microscope set up with ~1.6 dB optical loss. The p-i-n detector was fiber pigtailed, shielded in a metallic box, and had a coaxial cable connection. Polarization controllers (PCs) were used to account for the polarization mismatch and improved the shape and the peak height of the interference envelope. Outputs of the p-i-n and the EI photodetector were amplified simultaneously using voltage amplifiers. Electronic band pass filtering was implemented to improve the SNR. The signals were then digitized using a data acquisition board (DAQ). In this setup, the input referred noise of the amplifiers dominated the quantization noise of the DAQ.

The key parameters defining the system performance (see "Methods" section, equation (6), for details) were experimentally measured and are presented in Table 1 for both EI and p-i-n detectors.

TABLE 1

Key parameters defining the system SNR performance

| Parameter | Electron-Injection Photodetector | p-i-n Detector |
|---|---|---|
| $P_s$ (PW) | 160 | 320 |
| $i_{amp}$ (pA/√Hz) | 10 | 7 |
| $\eta_{ext}$ | 78% | 60% |

TABLE 1-continued

Key parameters defining the system SNR performance

| Parameter | Electron-Injection Photodetector | p-i-n Detector |
|---|---|---|
| $\eta_{int}$ | 100% | 100% |
| G (at 35 MHz) | 70 | 1 |
| F | 1 | 1 |
| $P_{RIN}$(dBc/Hz) | | −130.6 |
| BW (KHz) | | 100 |
| $P_0$ (mW) | | 0.89 |

Experimentally Measured Sensitivity in SS-OCT Setup.

Figure 5:
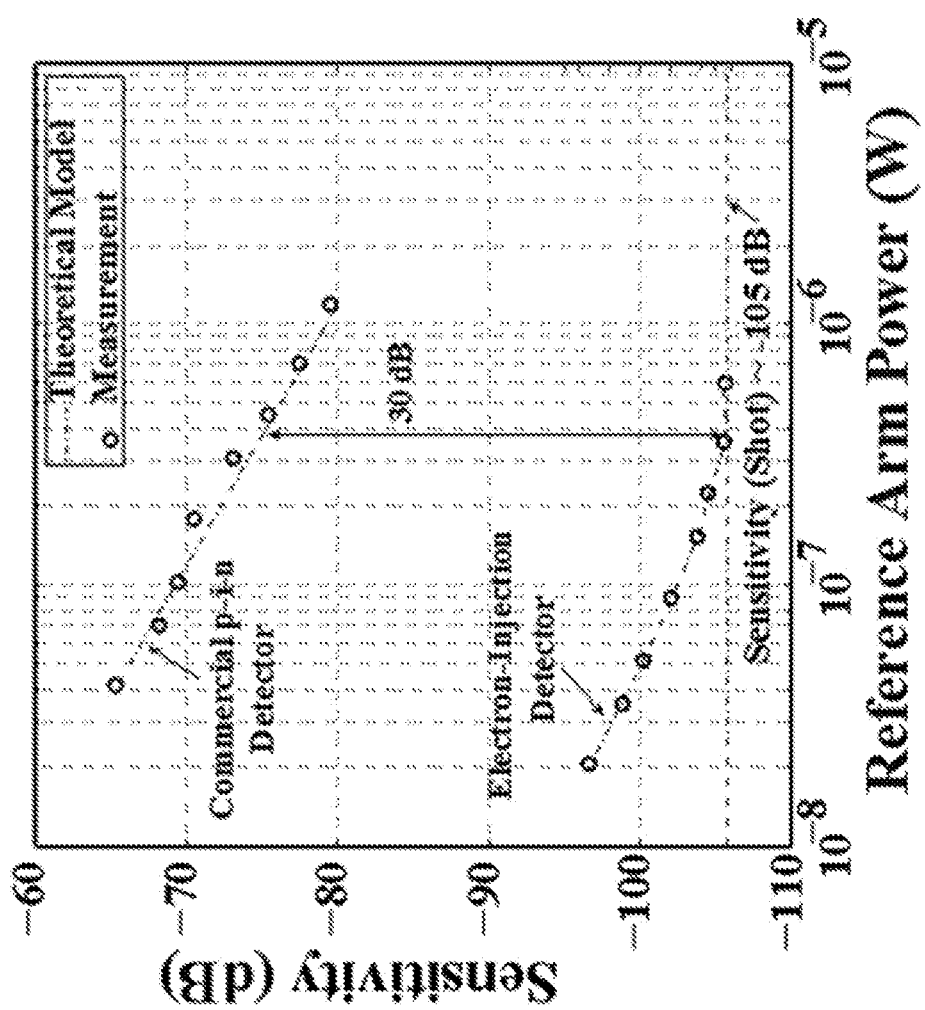
FIG. 5 shows a comparison of the measured and the theoretically calculated sensitivity as a function of the reference arm power for two single-ended detection schemes as shown in FIG. 4 (the EI photodetector and the commercial p-i-n detector). The symbols are experimental data and the curves are theoretically calculated. The EI photodetector yields ~30 dB higher sensitivity as compared with the commercial p-i-n detector. The sample power at the EI photodetector was ~160 pW. The gain in the EI photodetector amplified shot noise and allowed it to surpass the amplifier noise at a factor of $G^2$ lower reference power level as compared to the p-i-n diode. The EI photodetector reached shot noise limited sensitivity of −105 dB at a reference power level of 350 nW.

FIG. 5 shows the experimental results for sensitivities of the EI and the p-i-n detectors, measured simultaneously as a function of the reference arm power at the detectors. To determine the optimum reference arm power, the signal-to-noise-ratio of the detector was obtained from the Discrete Fourier Transform (DFT) of the sampled detector signals as a function of the reference arm power. The reference arm power at the EI photodetector varied from ~20 nW to ~600 nW using the variable neutral density filter placed in front of the reference mirror. The total attenuation level of the sample arm was ~67.5 dB, and the power returning from the sample at the EI photodetector was 160 pW. The experiment was performed at a beating frequency of 35 MHz.

As the reference arm power was increased, the SNR increased until it reached its maximum, dictated by the sample power returning to detector ($P_s$). The gain in this device amplified shot noise and allowed it to surpass the amplifier noise at a factor of $G^2$ times lower reference power compared to the p-i-n detector.

Utilizing the measured detector parameters provided in Table 1, and in Equation (4) of the "Methods" section, it can be concluded that the EI photodetector shot noise would surpass the amplifier noise (also provided in Table 1) at a reference power of 350 nW. This was confirmed experimentally in this SS-OCT system. As shown by the markers in FIG. 5, the measured sensitivity of the EI photodetector reached its shot-noise-limit of ~−105 dB (indicated by the dotted line and calculated from Equation (7) in the "Methods" section) at a reference power level of ~350 nW. This is believed to be the lowest reference power ever achieved for a shot-noise-limited operation in SS-OCT systems at room temperature. The typical optimum reference power level for a balanced detection system is in the few mW range [14, 15,34], with a lowest reported value of ~15 μW [17]. Furthermore, this is the first report of shot-noise-limited performance, without the use of balanced detection in an SS-OCT setup.

As shown in FIG. 5, an improvement in sensitivity of ~30 dB was obtained by the EI photodetector as compared to the commercial p-i-n detector. The theoretically calculated sensitivity curves, obtained from the measured data presented in Table 1, and using Equation (6) in the "Methods" section, are indicated by the dotted lines in FIG. 5.

The A-line profile at a reference arm power of 350 nW generated from the EI photodetector was also obtained (data not shown). The measured SNR of ~38 dB was in good agreement with the theory for shot-noise-limited SNR (Equation (6) in the "Methods" section). From the measured SNR, and the attenuation in the sample arm, the sensitivity of the system was confirmed to be about −105 dB. Furthermore, the experimentally measured noise data lay around the theoretically calculated noise power for this detector operating under a shot-noise-limited regime.

Using $P_0$, and the measured sensitivity, it can be concluded that the EI photodetector could respond to powers coming from the sample arm as low as 25 fW at a 35 MHz bandwidth. In this experimental setup, measurements at sample powers lower than 160 pW were limited by the non-ideal directivity of the coupler.

From the measured shot noise and the measured EI photodetector responsivity from Table 1, the NEP of the EI photodetector was confirmed to be about 300 fW/√Hz. This is similar to the value obtained from the homodyne approach.

The side lobes in the interference fringe envelope observed in the A-line profile, which were also present in the p-i-n detector spectra, may have been caused by the non-ideal Gaussian spectral shape of the source. Furthermore, the group velocity dispersion and polarization mismatch between the reference and the sample arms were factors that strongly affected the interference envelope [35].

The above OCT setup was designed to allow simultaneous evaluation of EI and p-i-n photodetectors. Therefore, it uses a high power swept source laser and an additional coupler. However, the results suggest that a compact OCT system with fewer components and significantly lower laser power can be realized. Current wavelength-swept VCSELs can provide up to a few milliwatts of optical power [36,37]. However, booster optical amplifiers (BOAs) are an integral part of almost any SS-OCT system today [38,39,40], since the VCSEL output power needs to be amplified to higher than 20 mW [39]. For applications that require few milliwatts sent to the sample arm, such as in ophthalmology, a system based on the EI photodetector could utilize a single VCSEL where almost all of the VCSEL power could be directed to the sample arm using a 99/1 coupler. These models predict that sensitivities of better than −100 dB could be obtained, using a single micro-scale electrically pumped VCSEL [41,42] and eliminating the need for optical power amplification. Such a system would also have a smaller footprint, and lower cost and complexity, as it would eliminate the need for utilizing two channels that require near-perfect matching with regard to the optical signals on each detector in different polarization, gain, and noise across the whole optical bandwidth [17, 21, 22].

For applications that require more than a few milliwatts of optical power on the sample arm, the reduced laser power might not necessarily be an advantage. In such applications, however, utilization of the EI photodetector would still make the system simpler, as it would eliminate the need for having two perfectly matched channels.

To conclude, progress towards a compact and low-cost swept laser source OCT system has long been limited by the lack of high performance detector technologies. EI photodetectors reduce the contribution of post-detection circuitry noise by several orders of magnitude so that it becomes irrelevant even at low optical powers. EI photodetectors have a cutoff wavelength of 1700 nm and operate at room temperature and low bias voltages. They provide a noise-free stable internal amplification mechanism with little excess noise. Using one such EI photodetectors, it was experimentally demonstrated for the first time that shot-noise-limited sensitivity in an SS-OCT system without balanced detection could be achieved. This was achieved at ~350 nW of optical reference power, which is believed to be the lowest power level reported in an SS-OCT operating at the shot-noise-limit. These experimental results show an excellent agreement with the theoretical calculations and suggest that an EI photodetector would eliminate the concomitant cost and complexity of current SS-OCT systems. This detection approach can be an enabling technology for portable OCT systems, allowing the use of a micron-scale tunable laser source (e.g. VCSEL) and a micron-scale detector.

REFERENCES

[1] Huang, D. et al. Optical coherence tomography, Science, 254, 1178-1181 (1991).

[2] Fujimoto, J. G., Pitris C., Boppart S. A., Brezinski, M. E. Optical coherence tomography: an emerging technology for biomedical imaging and optical biopsy, Neoplasia, 2, 9-25 (2000).

[3] Fujimoto, J. G., Optical coherence tomography for ultrahigh resolution in vivo imaging, Nature Biotechnology, 21, 1361-7 (2003).

[4] Choi, B. et al. Use of optical coherence tomography to monitor biological tissue freezing during cryosurgery, Journal of Biomedical Optics, 9, 282-6 (2004).

[5] Al-Mujaini, A., Wali, U. K., Azeem, S., Optical coherence tomography: clinical applications in medical practice, Oman Medical Journal, 28, 86-91 (2013).

[6] Cho, N. H., Jung, U., Kim, S., Kim, J., Non-destructive inspection methods for LEDs using real-time displaying optical coherence tomography, Sensors, 12, 10395-10406 (2012).

[7] Zhang, Q. et al. Wide-field optical coherence tomography based microangiography for retinal imaging, Scientific Reports, 6, 22017 (2016).

[8] Potsaid, B. et al. Ultrahigh speed 1050 nm swept source/Fourier domain OCT retinal and anterior segment imaging at 100,000 to 400,000 axial scans per second, Optics express, 18, 20029-20048 (2010).

[9] Low, A. F., Tearney, G. J., Bouma, B. E., Jang, I. Technology Insight: optical coherence tomography—current status and future development, Nature Clinical Practice Cardiovascular Medicine, 3, 154-162 (2006).

[10] Su, Y. et al. Measurements of the thermal coefficient of optical attenuation at different depth regions of in vivo human skins using optical coherence tomography: a pilot study, Biomedical Optics Express, 6, 500-513 (2015).

[11] Kang, H. et al. Nondestructive assessment of early tooth demineralization using cross-polarization optical coherence tomography, IEEE Journal of Selected Topics In Quantum Electronics, 16, 870-876 (2010).

[12] Otis, L. L., Everett, M. J., Sathyam, U. S., Colston Jr., B. W., Optical coherence tomography: a new imaging: technology for dentistry, The Journal Of The American Dental Association, 131, 511-514 (2000).

[13] Fujimoto, J. G. et al. Optical biopsy and imaging using optical coherence tomography, Nature Medicine, 1, 970-972 (1995).

[14] Rollins, A. M., Izatt, J. A. Optimal interferometer designs for optical coherence tomography," Optics Letters, 24, 1484-1486 (1999).

[15] Podoleanu, A. Gh., Unbalanced versus balanced operation in an optical coherence tomography system, Applied Optics, 39, 173-182 (2000).

[16] Mohan, N. et al. "Photon-counting optical coherence-domain reflectometry using superconducting single photon detectors," Optics Express, 16, 18118-18130 (2008).

[17] Yun, S. H., Tearney, G. J., de Boer, J. F., Iftimia, N., Bouma, B. E., High-speed optical frequency-domain imaging, Optics express, 11, 2953-2963, (2003).

[18] Chinn, S. R., Swanson, E. A., Fujimoto, J. G., Optical coherence tomography using a frequency-tunable optical source, Optics Letters, 22, 340-342 (1997).

[19] Grulkowski, I. et al. High-precision, high-accuracy ultra long-range swept-source optical coherence tomography using vertical cavity surface emitting laser light source, Optics Letters, 38, 673-675 (2013).
[20] Grulkowski, I. et al. Retinal, anterior segment and full eye imaging using ultrahigh speed swept source OCT with vertical-cavity surface emitting lasers, Biomedical Optics Express, 3, 2733-2751 (2012).
[21] Chen, Y., de Bruin, D. M., Kerbage, C., de Boer, J. F., Spectrally balanced detection for optical frequency domain imaging, Optics Express, 15, (2007).
[22] Kuo, W. C., Lai, C. M., Huang, Y. S., Chang, C. Y., Kuo, Y. M., Balanced detection for spectral domain optical coherence tomography, Optics Express, 21, 19280 (2013).
[23] Movassaghi, Y., Fathipour, V., Fathipour, M., Mohseni, H., Analytical modeling and numerical simulation of the short-wave infrared electron-injection detectors, Applied Physics Letters, 108, 121102 (2016).
[24] Fujiwara, K., Matoba, O., High-speed cross-sectional imaging of valuable documents using common-path swept-source optical coherence tomography, Applied Optics, 50, H165-H170 (2011).
[25] Shelton, R. L., et al. Optical coherence tomography for advanced screening in the primary care office, Journal of Biophotonics, 7, 525-533 (2014).
[26] Lu, C. D. et al. Handheld ultrahigh speed swept source optical coherence tomography instrument using a MEMS scanning mirror, Biomedical Optics Express, 5, 293-311 (2014).
[27] Drew, M., Li, D., Pacifici, D., Measuring subwavelength spatial coherence with plasmonic interferometry, Nature Photonics, 10, 681-687 (2016).
[28] Memis, O. G. et al. A photon detector with very high gain at low bias and at room temperature, Appl. Phys. Lett., 91, 171112, (2007).
[29] Fathipour, V., Jang, S. J., Nia, I. H., Mohseni, H., Impact of three-dimensional geometry on the performance of isolated electron-injection infrared detectors, Applied Physics Letters, 106, 021116 (2015).
[30] Memis, O. G. et al. Sub-Poissonian Shot Noise of a High Internal Gain Injection Photon Detector, Optics Express, 16, 12701, (2008).
[31] Data from "PDB460C, Thorlabs". Information available at (https://www.thorlabs.com/thorcat/21600/PDB460C-AC-Manual.pdf)
[32] Data from "EBR370006-02 EXALOS AG". Information available at (http://www.exalos.com/balanced-receivers/)
[33] Thorlabs: Balance Amplified Photodetectors (PDB410C, PDB420C, PDB440C, PDB460C), Available at: https://www.thorlabs.com/newgrouppage9.cfm?objectgroup_id=5201 #7259
[34] Sarunic, M. V., Choma, M. A., Yang, C., Izatt, J. A., Instantaneous complex conjugate resolved spectral domain and swept-source OCT using 3×3 fiber couplers, Optics Express, 13, 957-967 (2005).
[35] Gong, J. et al. Optimal spectral reshaping for resolution improvement in optical coherence tomography, Optics Express, 14, 5909-5915 (2006)
[36] Ansbaek, T., Chung, I. S., Semenova, E. S., Yvind, K., 1060-nm Tunable Monolithic High Index Contrast Subwavelength Grating VCSEL, IEEE Photonics Technology Letters, 25, 4, 365-367, (2013).
[37] Rao Y. et al. Long-Wavelength VCSEL Using High-Contrast Grating, IEEE Journal of Selected Topics in Quantum Electronics, 19, 4, 1701311-1701311, (2013).
[38] Jayaraman, V. et al. High-speed ultra-broad tuning MEMS-VCSELs for imaging and spectroscopy Proc. SPIE, 8763, 87630H (2013).
[39] Potsaid, B. et al. MEMS tunable VCSEL light source for ultrahigh speed 60 kHz-1 MHz axial scan rate and long range centimeter class OCT imaging, Proceedings of SPIE, 8213, 82130M (2012).
[40] More information on https://www.thorlabs.com/newgrouppage9.cfm?objectgroup_id=7109
[41] John, D. D. et al. Wideband Electrically Pumped 1050-nm MEMS-Tunable VCSEL for Ophthalmic Imaging, Journal of Light wave Technology, 33, 3461-3468 (2015).
[42] Yang, W., Gerke S. A., Ng, K. W, Rao, Y., Chase, C., Chang-Hasnain, C. J., Laser optomechanics, Scientific Reports, 5, (2015).
[43] Fathipour, V. et al. Isolated Electron Injection Detectors With High Gain and Record Low Dark Current at Telecom Wavelength, IEEE Journal of Selected Topics in Quantum Electronics, 20, 6, 65-70 (2014).

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A system for coherent light detection, the system comprising
   a light source configured to generate light;
   a first optical assembly comprising a first optic and configured to split the light into a reference arm and a sample arm;
   a second optical assembly comprising a second optic and configured to illuminate a sample with light of the sample arm, thereby generating a sample signal;
   a third optical assembly comprising a third optic and configured to combine the sample signal with light of the reference arm, thereby generating an interference signal; and
   a detector assembly comprising an array of carrier injection photodetectors, the array arranged to collect the interference signal, wherein each carrier injection photodetector comprises a semiconductor heterostructure comprising
   a photon absorber comprising a layer of photon absorbing material selected to absorb photons to generate electron-hole pairs therein; and
   a carrier injector configured to inject one of either electrons or holes into the photon absorber, the carrier injector comprising a layer of carrier injecting material selected to generate the one of either electrons or holes upon application of a bias voltage across the carrier injection photodetector and a carrier trap between the layer of carrier injecting material and the layer of photon absorbing material, the carrier trap comprising a layer of potential barrier-forming material selected to form a potential trap for the other of either electrons or holes generated in the photon absorber.

2. The system of claim 1, wherein the light source is configured to emit light having a wavelength in the short-wave-infrared region of the electromagnetic spectrum.

3. The system of claim 1, wherein the light source is a swept-source laser.

4. The system of claim 1, wherein the layer of carrier injecting material is configured to generate electrons and the layer of potential barrier-forming material is selected to form the potential trap for holes.

5. The system of claim 1, wherein the semiconductor heterostructure is composed of Group III-V semiconductors.

6. The system of claim 5, wherein the photon absorbing material is InGaAs, the carrier injecting material is n-type doped InP, and the potential barrier forming material is p-type doped GaAsSb or InGaAs.

7. The system of claim 1, wherein the layer of carrier injecting material has a maximum lateral dimension of greater than 1 µm.

8. The system of claim 7, wherein the layer of carrier injecting material has a maximum lateral dimension in the range of from about 5 µm to about 50 µm.

9. The system of claim 1, wherein each carrier injection photodetector is characterized by a gain in a range of from 50 to 2000 at a bias voltage of 1 to 3 Volts and a wavelength of 900 nm to 1700 nm at room temperature and a bandwidth in a range of from 5 MHz to 1 GHz.

10. The system of claim 9, wherein the gain is less than 300 and the bandwidth is less than 50 MHz.

11. The system of claim 1, wherein the array of carrier injection photodetectors is a linear array.

12. The system of claim 11, wherein the array comprises at least 10 carrier injection photodetectors.

13. The system of claim_11, wherein the array comprises at least 50 carrier injection photodetectors.

14. The system of claim 1, wherein the system is configured to perform parallel, line scan optical coherence tomography.

15. The system of claim 1, wherein the system is configured to perform coherent LiDAR.

16. The system of claim 1, wherein carrier injection photodetectors in the array exhibit a sensitivity of at least −95 dB at a reference arm power of $1 \times 10^{-8}$ W.

17. The system of claim 1, wherein the array of carrier injection photodetectors comprises at least 1024 carrier injection photodetectors.

18. A method of using the system of claim 1, the method comprising
splitting the light from the light source into the reference arm and the sample arm;
illuminating the sample with light from the sample arm, thereby generating the sample signal;
combining the sample signal with light from the reference arm, thereby generating the interference signal; and
collecting the interference signal on the array of carrier injection photodetectors.

19. A system for parallel, line scan optical coherence tomography, the system comprising
a light source configured to generate light, wherein the light source is a swept-source laser;
a first optical assembly comprising a first optic and configured to split the light into a reference arm and a sample arm;
a second optical assembly comprising a second optic and configured to illuminate a sample with light of the sample arm, thereby generating a sample signal;
a third optical assembly comprising a third optic and configured to combine the sample signal with light of the reference arm, thereby generating an interference signal; and
a detector assembly comprising a linear array of carrier injection photodetectors, the array arranged to collect the interference signal, wherein each carrier injection photodetector comprises a semiconductor heterostructure comprising
a photon absorber comprising a layer of photon absorbing material selected to absorb photons to generate electron-hole pairs therein; and
a carrier injector configured to inject one of either electrons or holes into the photon absorber, the carrier injector comprising a layer of carrier injecting material selected to generate the one of either electrons or holes upon application of a bias voltage across the carrier injection photodetector and a carrier trap between the layer of carrier injecting material and the layer of photon absorbing material, the carrier trap comprising a layer of potential barrier-forming material selected to form a potential trap for the other of either electrons or holes generated in the photon absorber.

20. The system of claim 19, wherein each carrier injection photodetector is characterized by a gain in a range of from 50 to 2000 at a bias voltage of 1 to 3 Volts and a wavelength of 900 nm to 1700 nm at room temperature and a bandwidth in a range of from 5 MHz to 1 GHz.

21. The system of claim 20, wherein the gain is less than 300 and the bandwidth is less than 50 MHz.

22. The system of claim 19, wherein the layer of carrier injecting material has a maximum lateral dimension in the range of from about 5 µm to about 50 µm.

\* \* \* \* \*